United States Patent
Helfmann et al.

(10) Patent No.: US 11,137,347 B2
(45) Date of Patent: Oct. 5, 2021

(54) OPTICALLY ASCERTAINING THE SUN PROTECTION FACTOR OF SUNSCREENS OR OTHER RADIATION PROTECTION AGENTS

(71) Applicant: Courage + Khazaka Electronic GmbH, Cologne (DE)

(72) Inventors: Jürgen Helfmann, Kleinmachnow (DE); Ingo Gersonde, Berlin (DE)

(73) Assignee: COURAGE + KHAZAKA ELECTRONIC GMBH, Cologne (DE)

( * ) Notice: Subject to any disclaimer, the term of this patent is extended or adjusted under 35 U.S.C. 154(b) by 0 days.

(21) Appl. No.: 15/769,892

(22) PCT Filed: Oct. 20, 2016

(86) PCT No.: PCT/DE2016/100491
§ 371 (c)(1),
(2) Date: Apr. 20, 2018

(87) PCT Pub. No.: WO2017/067545
PCT Pub. Date: Apr. 27, 2017

(65) Prior Publication Data
US 2018/0321139 A1   Nov. 8, 2018

(30) Foreign Application Priority Data
Oct. 20, 2015   (DE) ............... 10 2015 013 558.9

(51) Int. Cl.
*G01N 21/33* (2006.01)
*A61B 5/00* (2006.01)
(Continued)

(52) U.S. Cl.
CPC ........... *G01N 21/33* (2013.01); *A61B 5/0075* (2013.01); *A61B 5/0077* (2013.01);
(Continued)

(58) Field of Classification Search
CPC ...... G01N 21/33; G01N 21/49; G01N 21/474; G01N 2021/4742; A61B 5/0082; A61B 5/0077; A61B 5/0075; A61B 5/441
See application file for complete search history.

(56) References Cited

U.S. PATENT DOCUMENTS

| 4,749,865 A | * | 6/1988 | Scheller | A61B 5/0059 250/338.1 |
| 5,500,533 A | * | 3/1996 | Ogawa | A61N 5/06 250/372 |

(Continued)

FOREIGN PATENT DOCUMENTS

| CN | 1259040 | 7/2000 |
| CN | 101821604 | 9/2010 |

(Continued)

OTHER PUBLICATIONS

International Search Report issued by the European Patent Office in International Application PCT/DE2016/100491.

(Continued)

*Primary Examiner* — Mohamed K Amara
(74) *Attorney, Agent, or Firm* — Henry M. Feiereisen LLC (57) ABSTRACT

The invention is used to ascertain a sun protection factor for light, for example for cosmetics and sunscreens for which a sun protection factor (SPF) is specified. Two measurements of the light backscattering on the skin surface are carried out in vivo or in vitro or on skin models (animal skin models or artificial skin models) before and after applying the radiation protection means onto the skin, and the sun protection factor is ascertained therefrom. In contrast to standard methods used until now, the distance between the lighting surface and the detection surface on the skin is ascertained for the irradiation path of the measurement method. The skin lighting dose used during the measurement lies below harmful (Continued)

limits. The sun protection factor can be ascertained according to previous standards or for additional wavelengths or wavelength ranges (e.g. UVA, VIS, NIR, IR).

16 Claims, 3 Drawing Sheets

(51) Int. Cl.
*G01N 21/49* (2006.01)
*G01N 21/47* (2006.01)

(52) U.S. Cl.
CPC ............ *A61B 5/0082* (2013.01); *A61B 5/441* (2013.01); *G01N 21/474* (2013.01); *G01N 21/49* (2013.01); *G01N 2021/4742* (2013.01)

(56) References Cited

U.S. PATENT DOCUMENTS

| | | | |
|---|---|---|---|
| 5,640,957 A | 6/1997 | Kaminski et al. | |
| 6,025,284 A * | 2/2000 | Marco | D03D 1/007 428/409 |
| 6,348,694 B1 * | 2/2002 | Gershteyn | A61B 5/0059 250/372 |
| 6,615,061 B1 | 9/2003 | Khalil et al. | |
| 6,820,014 B2 * | 11/2004 | Ferrero | A61K 8/35 250/372 |
| 7,033,577 B2 * | 4/2006 | Dueva-Koganov | G01N 21/33 424/400 |
| 7,937,227 B2 * | 5/2011 | Miura | G01N 21/33 702/30 |
| 8,159,656 B2 * | 4/2012 | Miura | G01N 21/33 356/51 |
| 8,913,118 B2 * | 12/2014 | Millikan | G01J 3/0229 348/77 |
| 9,116,045 B2 * | 8/2015 | Lian | G01J 1/0403 |
| 9,579,040 B2 * | 2/2017 | Rafferty | A61B 5/0533 |
| 10,568,517 B2 * | 2/2020 | Millikan | A61B 5/0075 |
| 2003/0157039 A1 | 8/2003 | Ferrero | A61K 8/35 424/59 |
| 2004/0195519 A1 * | 10/2004 | Refregier | G01N 21/33 250/372 |
| 2004/0219684 A1 * | 11/2004 | Dueva-Koganov | G01N 21/33 436/171 |
| 2006/0244961 A1 * | 11/2006 | Cole | A61B 5/0071 356/319 |
| 2007/0038041 A1 | 2/2007 | Yang et al. | |
| 2008/0088776 A1 * | 4/2008 | Ishigaki | G02F 1/13439 349/114 |
| 2010/0012850 A1 * | 1/2010 | Miura | A61B 5/0059 250/372 |
| 2010/0014069 A1 * | 1/2010 | Miura | G01N 21/33 356/51 |
| 2010/0256924 A1 * | 10/2010 | Miura | G01N 21/33 702/30 |
| 2012/0022472 A1 * | 1/2012 | Miura | A61B 5/0059 604/290 |
| 2013/0200268 A1 * | 8/2013 | Rafferty | H04Q 9/00 250/372 |
| 2013/0245388 A1 * | 9/2013 | Rafferty | A61B 5/4266 600/301 |
| 2015/0108360 A1 * | 4/2015 | Stanfield | G01N 21/255 250/372 |
| 2015/0177063 A1 * | 6/2015 | Lian | G01J 1/0403 250/372 |
| 2015/0308945 A1 * | 10/2015 | Hanyu | G01N 21/59 250/372 |
| 2015/0335254 A1 * | 11/2015 | Fastert | A61B 5/6833 600/549 |
| 2016/0313236 A1 | 10/2016 | Helfmann et al. | |
| 2017/0108433 A1 | 4/2017 | Helfmann et al. | |

FOREIGN PATENT DOCUMENTS

| | | |
|---|---|---|
| CN | 102811703 | 12/2012 |
| CN | 103025333 | 4/2013 |
| DE | 19828497 A1 | 12/1999 |
| DE | 102004020644 A1 | 11/2005 |
| EP | 0810429 | 12/1997 |
| WO | WO 2007/100648 A2 | 9/2007 |

OTHER PUBLICATIONS

Ruvolo E; Kollias N; Cole C "Photodermatol Photoimmunol Photomed" vol. 30, 2014, pp. 202-211.
R. Gillies et al: "Non-invasive in vivo determination of UVA efficacy of sunscreens using diffuse reflectance spectroscopy".
Chinese Search Report dated Dec. 6, 2020 with respect to counterpart Chinese patent application 2016800747267.
Translation of Chinese Search Report dated Dec. 6, 2020 with respect to counterpart Chinese patent application 2016800747267.

* cited by examiner

OPTICALLY ASCERTAINING THE SUN PROTECTION FACTOR OF SUNSCREENS OR OTHER RADIATION PROTECTION AGENTS

CROSS-REFERENCES TO RELATED APPLICATIONS

This application is the U.S. National Stage of International Application No. PCT/EP2016/100491, filed Oct. 20, 2016, which designated the United States and has been published as International Publication No. WO 2017/067545 and which claims the priority of German Patent Application, Serial No. 10 2015 013 558.9, filed Oct. 20, 2015, pursuant to 35 U.S.C. 119(a)-(d).

BACKGROUND OF THE INVENTION

The invention describes a method for the qualification of cosmetics and sunscreens for which a sun protection factor (SPF) or a still to be redefined protection factor is specified.

The current methods approved by the European Union (EU) and the US Food and Drug Administration (FDA) for the determination of SPF are all harmful to the test subjects, because they cause erythema, i.e. a light-induced skin inflammation (COLIPA—European Cosmetic, Toiletry and Perfumery Association: Colipa SPF Test Method 941289, 1994; ISO standards 24442, 24443, 24444). Therefore, both the FDA and the EU have repeatedly pointed out that future research activities must be directed towards new methods for characterizing the protective effect of sunscreens in order to avoid long-term consequences for the test subjects (European Commission, Standardization Mandate Assigned to CEN Concerning Methods for Testing Efficacy of Sunscreen Products, M/389 EN, Brussels, 12 Jul. 2006). This object is to be achieved with this invention.

The existing procedures are defined in various references:
I. Procedures Defined in Standards and Regulations:
 a. ISO 24444 defines a method for the in-vivo determination of SPF. The basis of the method is the generation of erythema on the skin of test subjects by radiation in the UVB-range. Thus, the process is harmful. In order to reduce the dependency of the result on inter-individual variations of the skin characteristics, the procedure must be carried out on several test subjects.
 b. ISO 24443 defines an in-vitro method for determining the UVA protection factor (UVAPF). The sunscreen is applied to a plastic plate so that a transmission spectrum of the sunscreen can be measured. Due to uncontrollable variations of the procedure, the transmission spectrum is adjusted by scaling to the result of the erythema test according to ISO 24444 and thus depends on its execution. The plastic plate used has a roughened surface and is thus a relatively unrealistic skin model.
 c. ISO 24442 defines an in-vivo method by which the UVA protection factor is determined with the minimum dose of UVA that generates an irreversible pigmentation (tanning) of the skin. This procedure, too, causes a change in the skin of the test subject.
 d. FDA Final Rules 201 1, originally published in the Federal Register of 27 Aug. 2007 (72 FR 49070) and codified as Broad Spectrum Test (21 CFR 201.327 (j)) and Sun Protection Factor (SPF) test (21 CFR 201.327 (i)) or in one newer version as 21 CFR 201.352 (http://www.ecfr.gov/cgi-bin/textidx?SID=5555a0dd8b6d83a8570676d9a44bb6ef&mc=true&node=pt21.5.352&rgn=div5)

II. Patented Methods:
 a. DE 198 28 497 A1 describes a method in which, as in ISO 24444, erythema is produced in test subjects exposed to UV irradiation of the skin; in contrast to ISO 24444, these are detected by reflection spectroscopy. The process is thus also harmful; the optical effect (protection) of the sunscreen is not detected by direct optical measurements, but by a biological reaction of the body.
 b. DE 10 2004 020 644 A1 describes a method in which the generation of radicals by UV exposure in-vivo is measured quantitatively by way of electron spin resonance (ESR). Again, the optical effect of the sunscreen is here only indirectly detected. In addition, the measurement of the ESR is technically complex and requires relatively large, stationary devices (tabletop devices). They are also sensitive to interference from high-frequency radiation or rapid temporary magnetic field changes, such as electrical switching processes.
 c. With respect to the technology of WO 2007/100648, it is to be noted that, although distance-dependent measurements from a light source are also described, they are not included as a sole feature in the scope of the protection (only claim 3 names this distance, but refers back to claim 1 via claim 2). The characteristic feature likely depends on the angle of incidence because the distance-dependent measurement of backscatter with this basic arrangement is known from many references for over 30 years and thus is or cannot be protected: A. Ishimaru, Single Scattering and Transport Theory, Vol 1 (1978), Academic Press, p. 185 ff.

III. Publications:
 a. In Bendova H, et al., Toxicology in-vitro (2007), 1268-1275, methods of transmission spectroscopy using different films as skin models are compared. The determined protection factors depend strongly on the film used, a significant correlation of the protection factors with the SPF from ISO 24444 was not found.
 b. In Ruvolo E, Kollias N, Cole C, Photodermatol Photoimmunol Photomed (2014), 30: 202-2111 presents a method combining UVB transmission measurement with plastic substrates and an in-vivo backscatter measurement on the skin in the UVA region. The transmission measurement is adjusted to the UVA backscatter measurement by scaling, and good agreement with the in-vivo test of the SPF according to ISO 24,444 is achieved. The measurement arrangement for the UVA backscatter measurement contains a fiber bundle, which is placed on the skin. The measurement takes place via a plurality of illumination and detection fibers having different distances from each other. Since the sum of the light powers from the detection fibers is detected, no defined distance between the illumination surface and the detection surface is provided, but rather a summation of all distances. In the method according to the invention, the backscattering is measured at several well-defined distances.
 c. In Sohn M, Grain V, Imanidis G, Skin Pharmacol Physiol, (2015), 28: 31-41, skin from pig's ear is tested as a substrate for in-vitro transmission measurements. In comparison to the measurement with standardized plastic carriers, a better correlation results with the SPF determined in-vivo is obtained. This demonstrates that a realistic skin model is essential for the determination of protective factors. The transmission measurement was carried out with/without sunscreen. However, the error of such a measurement is strongly dependent on the used layer thickness (thickness of the separated layer of the pig's ear) and the surface roughness relative to the change by the (identical, normalized) amount of sunscreen and is in the measurements of the publication evaluated only against the SPF evaluated in-vivo according to ISO 24444:2010, not among themselves. Also, only one type of sunscreen agent (oil-in-water) was used, which has particularly high scattering properties due to oil droplet formation, thus making the surface changes less effective.

The field of application of the previous methods with UVB radiation (solar simulator, also "solar simulator" with predetermined wavelength-specific intensity between 290 to 400 nm corresponding to solar irradiation at sea level) and with limited opportunities with UVA radiation (erythema does not occur as with UVB, higher penetration depth than UVB into the skin=larger volume) should be extended with the inventive solution without restriction to the UVA, UVB, the visible and near-infrared or infrared range for the determination of appropriate sun protection factors.

Disadvantages of Previous Methods

For a number of important reasons, the process according to the invention is not only desirable but urgently required:

Increased doses of UV radiation can damage tissue and cellular components. Skin aging and, at worst, skin cancer are known to be the consequences. For decades, an increasing number of new cases of skin cancer has been observed, which currently stands at around 20,000 cases per year in Germany. The main cause is a recurring intense UV exposure, as occurs during summer vacations, especially in childhood and adolescence.

Existing procedures (also state of the art) for the evaluation of sunscreens are inadequate because they are either tested on the test subject invasively by forming erythema or are tested non-physiologically by using plastic substrates as a skin model.

Today's in-vivo SPF determination has a number of shortcomings. This determination only relates to a spontaneous biological effect (forced sunburn) caused by UVB radiation. However, it is known at present that the UVA radiation can also lead to severe skin damage and even skin cancer. In addition, the determination of the SPF is an invasive procedure, as it causes damage in the test subjects in the form of sunburn. Therefore, both the US Food and Drug Administration (FDA) and the European Union have repeatedly stated that future research activities must be directed towards new methods of characterizing the protective effect of sunscreens in order to avoid long-term consequences for the test subjects.

The in-vivo SPF can only be detected in UVB, whereas long-term damage is also caused by other spectral regions.

The addition of anti-inflammatory substances in sunscreens which make the in-vivo SPF more acceptable, has no influence on a purely physical measurement (e.g., in-vitro), as corresponding to the method according to the invention, thus preventing falsification of the SPF.

The existing in-vitro SPF method for UVA determines in a non-physiological, non-biological matrix for a plastic support only the SPF in the UVA and is thus totally inadequate for evaluating the in-vivo behavior during penetration and the distribution of the sunscreen. Furthermore, a parallel invasive in-vivo measurement is necessary for its determination in order to subsequently adapt the inaccurate measurement method in the UVA.

Basically, for example, an in-vivo-SPF measured in accordance with the COLIPA protocol indicates only the effectiveness of UVB protection, while the UVA component of sunlight is not adequately taken into account. Since harmful effects due to UVA radiation are also well known, it has been found necessary to establish a general test procedure for determining the UVA protection. This is due to the fact that the UV component of the solar radiation reaching the Earth's surface consists of about 5% UVB and about 95% UVA.

In-Vivo Situation for SPF Determination in the UVA

To date, three in-vivo methods have been described for determining UVA protection, IPD (Immediate Pigment Darkening), PPD (Persistent Pigment Darkening) and UVA-PF (UVA Protection Factor). While the IPD method does not always provide accurate readings, the PPD reaction has proven stable and reproducible. However, its clinical significance was considered questionable because the PPD action spectrum is not well defined for wavelengths below 320 nm, and other UV-induced skin reactions can also be superimposed on the PPD response. The UVA-PF method is based on "Minimal Erythematous Responses" and the persistent pigmentation caused by UVA. The COLIPA Guidelines from 2009 offer a detailed compilation of the PPD- and erythema action spectra as well as the UVA and UV-SSR (ultraviolet solar simulated light) spectral irradiance in the range 290-373 nm.

In-Vitro Situation for SPF Determination in UVA

A comprehensive list of current in-vitro protocols for SPF testing is provided by an Application Note on UV/VI S spectrometry from Perkin Elmer:

AS/NZS 2604 Broad Spectrum (2012) The new version of this is based on the test method described in ISO 24443 'Determination of Sunscreen UVA Protection In vitro'. UVAPF Ratio and critical wavelength requirements are calculated in order to arrive at Broad Spectrum compliance.

ISO-24443 (2012) Determination of Sunscreen UVA Protection in vitro. Determines both UVAPF Ratio and Broad Spectrum Compliance. Compliance with AS/NZS 2604.

SO 24442 (2012) This method is being adopted as the harmonized method for determination of UVAPF in vitro and for use in AS/NZS 2604 and Cosmetics Europe, ASEAN and other regions.

UVA-UVB Ratio (2010) Absorption of a 1.3 mg/Square cm film is measured between 290 nm and 400 nm. The ratio of areas under the curve between 290-320 (UVB region) is compared with the area under the curve between 320 nm and 400 nm. Pre-irradiation of the sample is required. (Calculated as TPF×UVA/UVB). Various Substrates can be nominated.

Boots Star Rating (2011) The method used by Boots in the UK (not mandated). Absorption of a 1 mg/square cm film is measured between 290 nm and 400 nm. Pre Irradiation of the sample is required. Rating scale is 3 to 5 stars. More stars mean more protection (by ratio) in the UVA area.

FDA, Final Rule 2011 The current proposed method for the USA. Absorption of a 0.75 mg/square cm film is measured between 290 nm and 400 nm. The critical wavelength is the point where 90% of the area under the curve lies, starting at the UVB end. Pre-irradiation of the sample is required.

DIN 67502 (UVA Balance) The methodology is based on that described in the German Standard DIN 67502. The SPF is determined using the values provided in the CIE. The SPF is applied in order to correct the values obtained in vitro. The PPD are derived by applying the values from the PPD Action Spectrum given in the Standard.

COLIPA (UVAPF) (2011) UVAPF/SPF Ratio and Critical Wavelength are calculated from this measurement technique. Compliance with E.U. requirements is also reported.

Radical Protection Factor

Radical Protection Factor (RPF) is the determination of free radicals generated by solar radiation in human skin. However, this method again has the disadvantage that it can only be carried out in-vivo using solar simulators, since in-vitro samples which are not perfused have a significantly lower oxygen concentration. However, oxygen is the basis for the formation of free radicals. The radical protection factor and the sun protection factor differ.

Medical/Technical/Objective Advantages and Disadvantages of Competitive Procedures The main disadvantage of sunscreen measurements in-vivo is the prevention of skin damage of the test subjects. The UVB sun protection factor can currently be reliably measured only by generating a slight sunburn, i.e. an inflammation of the skin. A similarly meaningful—albeit damaging—in-vivo-method is not available for the UVA.

However, harm to a test subject should generally be avoided. This is the main reason why in-vitro methods have been developed. The other reason is the extension of the SPF determination to the UVA. This means that there is an urgent need for in-vitro-methods that must come close in the reliability of the in-vivo methods.

However, the existing in-vitro methods have serious shortcomings, which need to be addressed:

In-Vitro Methods on Artificial Substrates
Different application, penetration, wetting and thus distribution behavior
No biological variability
Light distribution during the measurement does not correspond to the in-vivo situation
This is evident from the necessary but very artificial adaptation to the in-vivo UVB-SPF, which must be applied (whereby damage is not avoided). For high and low SPF the in-vitro determination deviates strongly from the expectation.

In-Vitro Method on Biological Substrates (Skin Tissue), e.g. Pig's Ear
Penetration and distribution behavior different from life human skin
Tissue samples must be laboriously prepared in thin layers for the measurement. Changes in the sample due to thermal or chemical preparation are to be expected, leading to poor repeatability due to handling difficulties.

By performing the measurements on an intact biological model tissue and taking into account the light distribution both in the measurement for SPF determination as well as in the real situation for protecting the skin from radiation, the above-mentioned problems and weaknesses should be overcome with this measuring method according to the invention.

| Risks | Measures for limiting risk |
|---|---|
| There are optical by-passes (crosstalk) which interfere with an unambiguous SRR measurement | With the design options on the fiber applicator (metallized fibers, recording plate with light barriers) and handling (defined contact pressure), the risk can be minimized. Residual crosstalk can (if constant) be detected and subtracted by measuring a dark standard. |
| The extreme differences in the light propagation without and with sunscreens do not allow a closed algorithm for SPF determination | Investigations in the visible have shown that rather small absorption coefficients ($\mu_a$ <0.04 mm$^{-1}$) are problematic. The SRR method or its reduction into optical properties can resolve two orders of magnitude for larger $\mu_a$. Two orders of magnitude can also be resolved for the reduced scattering coefficient (Andree et al., J. Biomed Opt 15 (6) (2010)). |
| The evaluation is problematic due to the big differences between the optical properties in the different layers of the skin. | The light propagation can be controlled by choosing the right distance range between the light source and the detection spot for the SRR. The signal is composed of a transmission almost perpendicular to the layers at entry and exit and a horizontal transmission determined by the distance. This allows the calculation of the diffuse transmission through the layer with/without sunscreen. It may be necessary to realize different optimum distance ranges in the fiber measuring head for the different wavelength ranges. |
| The influence of the corneal layer on the measurement is small compared to the influence of the remaining epidermis and the dermis, so that the signal contrast due to variations in the optical properties of the corneal layer is too small. | By selecting the distance for the SRR, the proportion of the different skin layers on the signal is changed. To become particularly sensitive in relation to the cornea, very small distances need to be realized which are technologically challenging. |
| The signals are too small for a large SPF, and the required dynamics of the measurement with/without is too large. | A very wide dynamic range can be detected by varying the integration time of the measurement, since the detector signals are linear with the integration time. |

| Risks | Measures for limiting risk |
| --- | --- |
| The SPF is locally too heterogeneous. | With the redundant measurement with several fibers for the same distance r, averaging can lead to a stable result. In addition, some heterogeneity is physiologically realistic and should be reproduced by the tissue model. The degree of heterogeneity can also be measured spatially resolved and provide valuable information about the distribution behavior of the sunscreen. |

BRIEF DESCRIPTION OF THE DRAWING

Figures

DETAILED DESCRIPTION OF PREFERRED EMBODIMENTS

Invention

It is therefore an object of the invention to provide a method and a device, which at least partially remedy the stated disadvantages of the prior art and which, in particular, reduce the stress on the measuring body due to the irradiation, while at the same time continue to provide high-quality analysis results.

According to one aspect of the invention, the object is achieved by a method for non-invasive determination of the sun protection factor of a radiation protection agent, the method including controlling at least one radiation source by a controller for emitting radiation to a measuring body, emitting radiation from the at least one radiation source, wherein the controller controls the at least one radiation source in such a way that the at least one radiation source emits a maximum light dose of smaller than MED and/or MZB, wherein the radiation source emits light at least in the range in which the protective effect of the sun protection factor is to be defined, detecting the radiation emitted by the radiation source in at least one detector, wherein a measurement cycle comprises several individual measurements, wherein the radiation emitted by the at least one radiation source is detected by at least one detector in at least two individual measurements, wherein the distance between the radiation source and the detector of the first individual measurement is different from the distance between the radiation source and the detector of the second individual measurement, analyzing the detected radiation while taking into account the respective distances between the radiation source and the detector.

According to another aspect of the invention, the object is achieved by a device for non-invasive determination of the sun protection factor of a radiation protection agent, the device including a sensor unit, the sensor unit including a) at least one radiation source and two detectors, wherein the detectors have different distances to the radiation source, or b) at least two radiation sources and one detector, wherein the radiation sources have different distances to the detector, or c) one radiation source and one detector, wherein the distance between the radiation source and the detector is variable, wherein the radiation source is adapted to emit light in the range in which the protective effect is to be defined, wherein the distances between the individual radiation sources and the detectors are defined, a controller for controlling the radiation source, wherein the controller is adapted to control the radiation source such that the radiation source emits a maximum light dose of small MED and/or MZB, an analysis unit adapted to analyze the detected radiation by taking into account the respective distances between the radiation source and the detector, an output unit that outputs the determined value.

The measuring method according to the invention enables the damage-free determination of protective factors of formulations for light and radiation protection on tissue (skin) in-vivo or in-vitro or also on skin models (animal skin models or artificial materials). This is achieved by evaluating two measurements of the light backscatter on the skin surface before and after applying the radiation protection agent to the skin. In contrast to previous methods, the distance between the illumination surface and the detection surface on the skin is defined with the aid of the beam path of the measuring method. The exposure dose of the skin used in the measurement is below the damage limit, which is usually stated as MED for the UVB range or by way of MZB values for the other wavelength ranges.

The irradiation takes place with at least one radiation source which emits relevant radiation at least in the wavelength range for which the protective effect or the SPF is to be defined. Alternatively, the radiation source can emit only a smaller wavelength range of the radiation relevant for the protective effect and determine by way of correlation measurements, which precede the determination according to the invention, the existing radiation protection or sun protection factor. The emitted radiation is detected by at least one detector, wherein the detection area has a defined distance from the measurement location of the point of incidence of the radiation source. The measuring cycle for determining the existing radiation protection or SPF consists of at least 2 individual measurements, wherein the radiation emitted by the radiation source of the illumination is transmitted through the measuring body (in addition to the layer modified by the applied radiation protection means) and strikes the detector, wherein the distance between the illumination surface and the detection surface on the measuring body between the measurements is predetermined, but different. A downstream device detects the at least two detector signals, amplifies these possibly with different degrees of amplification, and analyzes the signal level with an algorithm that determines a sun protection factor. The advantages of this method lie in the absence of damage to the test subject during in-vivo measurements, in the simple recalculation without taking into account the incident light power which must be constant only during the measurements with/without radiation protection, and also in the independence of the chosen distance between irradiation/Illumination and detection, and the independence on the existing skin type under the radiation protection or optical properties of the measuring body or skin model used. The advantage of the measurement is that any spectral intensities in the radiation sources can be used, which thus no longer require a calibrated "solar simulator". The detection can be carried out with simple detectors, which only have to output a signal above the noise, depending on the definition of the sun protection factor for the transmitted radiation for the worst case scenario of maximum light attenuation caused by radiation protection means and measuring body.

The method according to the invention provides the best results when the radiation protection agent to be tested is present as a thin layer and attenuates the transmitted radiation (see point 1 below). The attenuation by the radiation protection agent can then be described approximately by a scalar transmission factor T. This yields for the radiation density $\phi$ in deeper areas of the skin (depth z)

$\phi_{without}(z) = P_{in}L(z)$ without protection agent $\phi_{with}(z) = P_{in}TL(z)$ with protection agent (1)

$P_{in}$ denotes the illumination power, $L(z)$ the path-length-dependent light attenuation of the radiation through the skin. The sun protection factor (PF) is defined by the attenuation of the radiation density in the skin which is independent of z:

$$PF := \frac{\Phi_{without}(z)}{\Phi_{with}(z)} = \frac{1}{T} \quad (2)$$

Figure 2:
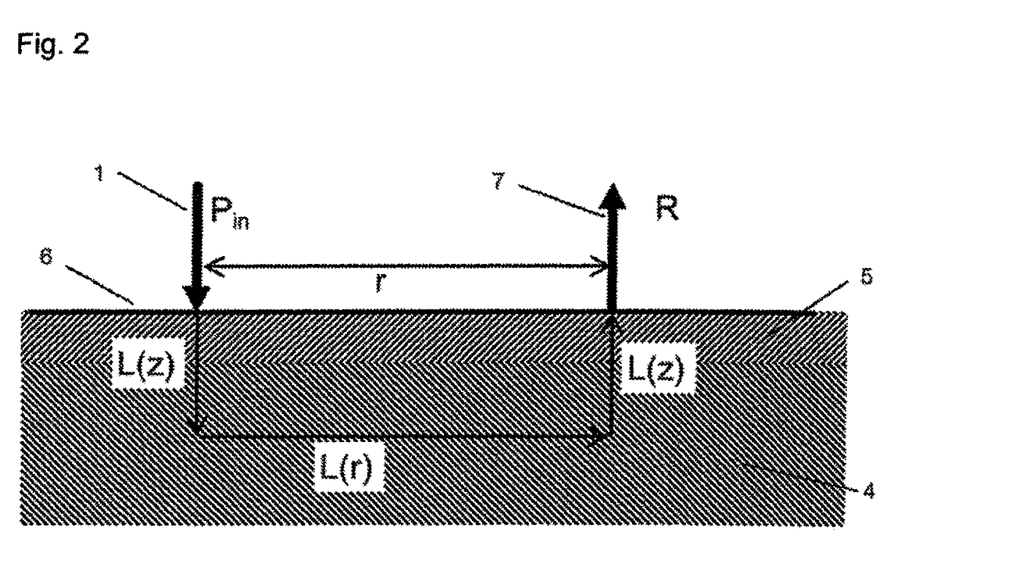
FIG. 2 shows the explanations for the derivation of the backscatter measurement according to the invention

The solution approach for determining PF is composed of determining the transmission factor T by way of backscatter measurements, since the transmission through the skin with and without protection agent layer cannot be detected directly, Here, light is irradiated locally into a limited exposure area of the skin surface, A portion of the light is remitted by scattering processes of the skin and measured in the area of a detection area Between the detection surface and the illumination surface there is a distance r, which, according to the invention, is chosen to be substantially greater than the layer thickness formed by the radiation protection agent. If the distance r is greater than the layer thickness formed by the radiation protection agent, the radiation transport from the illumination position to the detection surface can be described approximately by three sequential processes:

i. Transmission through skin layer with the applied radiation protection agent with a transmission factor T
ii. Lateral transmission through the deeper region $z \approx z_{across}$ of the skin, described by the light attenuation $L(r)$
iii. Repeated transmission through layer with the applied radiation protection agent with a transmission factor T.

The detected backscatter $R_{without}$ or $R_{with}$ thus becomes approximately $R_{without} = P_{in}L(r)L(z_{across})$ $R_{with} = P_{in}TL(z_{across})L(z_{across})T'$, wherein $T \approx T'$ (3)

Equations (2) and (3) can be used to calculate the sun protection factor PF from backscatter measurements before and after applying the radiation protection agent:

$$PF = \frac{1}{T} = \sqrt{\frac{R_{without}}{R_{with}}} \quad (4)$$

The ratio $R_{without}/R_{with}$ is independent of the distance r and of $z_{across}$. The backscatter is measured spectrally resolved. Protection factors corresponding to the existing standards can then be derived with the resulting spectrum of the transmission factor $T(\lambda)$.

For example, for the SPF one obtains:

$$SPF = \frac{\int I(\lambda)E(\lambda)d\lambda}{\int I(\lambda)E(\lambda)T(\lambda)d\lambda} \quad (5)$$

$I(\lambda)$ is the intensity spectrum of the sun and $E(\lambda)$ is the erythema spectrum, i.e. the spectra with an intensity sufficient for erythema formation. Other light sources with an illumination spectrum $I(\lambda)$ or a wavelength range $E(\lambda)$ to be protected by the radiation protection agents result analogously in protective factors, which can likewise be determined according to the invention.

Figure 3:
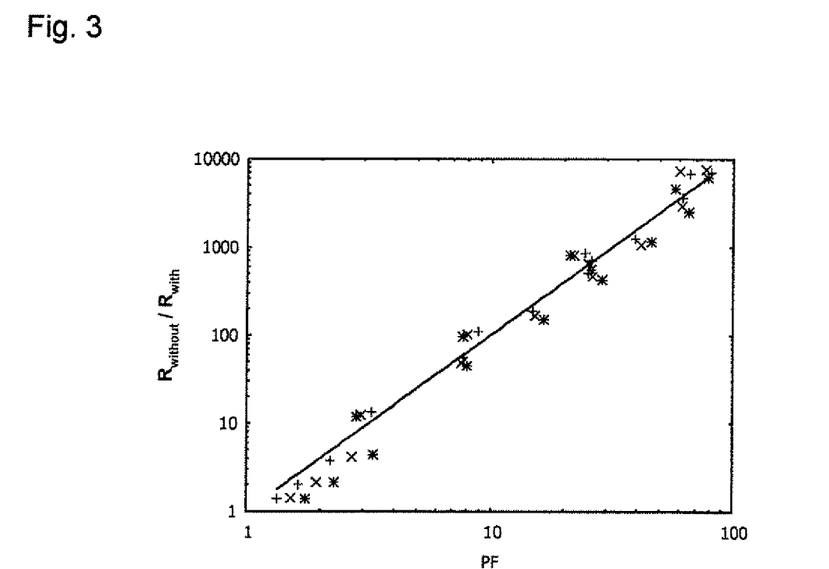
FIG. 3 shows model calculations on a skin model for the correlation of protection factor and backscatter. The indicated line corresponds to equation (4).

The relationship between backscatter and protection factor according to equation (4) can be confirmed with mod& calculations for UV light on a skin model. Radiation protection agents with varying scattering and absorption properties were assumed and furthermore the melanin content of the epidermis was varied. It turns out that the backscatter measurement described here is approximately independent of the special properties of the radiation protection agent, which is not the case for the methods of backscatter measurement described in the prior art 1. If the lateral distance r between the illumination surface and the detection surface is too small or if the radiation protection means have small sun protection factors, a portion of the light can be transmitted transversely through the corneal layer without having completely traversed the corneal layer in the vertical direction. This results in a deviation from the relationship described in equation (4). The minimum value for r results from the optical properties of the skin and the radiation protection agent. This minimum value is then r=0, from which a sun protection factor can already be determined. Preferably, the minimum value for r is the layer thickness of the radiation protection agent, which results in about 20 μm for the standardized application of sunscreen, and most preferably, the minimum value r is r=60 μm for UV light on the skin. A maximum value for r results from the amount of radiation still striking the detector, Le, the effect of the light attenuation by the radiation protection means AND the underlying skin, A practical value of 1 mm will here represent an upper limit for UV irradiation/protection formulation. Preferably, a maximum value for r is 500 µm. More preferably, a value of r is r≤200 µm, According to the invention, several re-emission measurements are recorded simultaneously with different values of r. For sufficiently large distances r, the attenuation T is independent of r, so that measurements having an exceedingly small distance can be detected and excluded from the evaluation in order to avoid an erroneous determination of the PF.

2. As a further measured value, the backscatter $R^0$ in the area of the illumination surface can be measured. Equation (4) can be augmented by a correction term g when using this measurement value, which reduces errors in the prediction of the PF. Thus, the formula for determining a corrected sun protection factor is:

$$PF = \sqrt{\frac{R_{without}}{R_{with}}} + g(R^0_{without}, R^0_{with}, R_{without}, R_{with}) \quad (6)$$

3. The skin has furrows and gaps which lead to a laterally inhomogeneous application of the radiation protection agent and thus to a location-dependent fluctuation of the sun protection factor and also influence the backscatter due to different skin formation in this area. These influences are only recorded when taking measurements on the skin. The methods mentioned in the prior art, which are based on PMMA substrates, do not detect this at all or only in a limited way in the case of embossed structures. In one embodiment of the solution according to the invention, a localized re-emission measurement is carried out with which this heterogeneity of the transmission can be determined by multiple measurements at adjacent positions. Thus, on the one hand, by suitably averaging, an average attenuation and thus an average PF can be determined. On the other hand, the variance of the attenuation can be determined, so that properties of the radiation protection agent with respect to the application to the skin can be examined.

Therefore, a method for further qualification can be provided by the described measuring method for describing the wetting behavior, the abrasion behavior and the distribution of the radiation protection agent over its useful life.

Due to the direct measurement of the optical effect of the radiation protection agent, the method described herein has a wider field of application in comparison to existing methods which use formation of erythema, pigments or radicals. In contrast to the existing procedures, a sample can be repeatedly measured; once induced erythema or pigmentation cannot be generated repeatedly. Furthermore, the sun protection factor can be detected spectroscopically in all required wavelength ranges.

In a separate embodiment of the measuring method, the measurements are performed sequentially at the same location on the measuring body, e.g. the skin. The measurements are hereby performed continuously for short periods of time and for longer periods of time with measurement pauses, wherein the optical interface of the measuring device is removed from the measuring site and periodically returned to the same location. Since the measurement does not change the skin (redness) or measuring body, the advantage of the procedure is that it can be carried out repeatedly at the same measuring site without falsification of the measured values. If multiple measurements are made, on the one hand the progress of the protective effect can be observed, which is not done with previous MED-based methods with invasive measurements for ethical reasons due to the large number of test subjects/sample sites. Measurement cannot be performed at the same location with the MED-based procedure because the determination is based on the appearance of redness, which however does not (as in sunburn) decrease in relevant protection periods (hours). Furthermore, the skin is pre-damaged at the measuring site and does not provide reliable information about the duration until damage occurs, until a complete regeneration (days).

In a separate embodiment of the measuring method, the measurement is carried out at measuring sites loaded with different amounts and/or types of radiation protection agent, or after interaction with the applied radiation protection agent at the same measuring site. This is done by removing the optical interface of the measuring device, applying additional radiation protection agent or an interaction at the measuring site (wiping/rubbing with a defined procedure, rinsing with water or the like, bleaching with light, etc.) and performing a further measurement, which is based on the original measurement without radiation protection agent. It is also conceivable to relate the measurement to the measurement carried out before the interaction. Advantage of the method is the detection of mechanical effects on the radiation protection and the possibility to more easily quantify such effects at the same location (e.g. back, as is customary, or forehead). For a reliable quantification, a group of test subjects must currently be measured, whose individual measured values must be separated by statistical evaluation from the influences caused by the interaction. Only with the method according to the invention is it possible to carry out a rapid measurement of interactions on the same measuring body and measuring site, respectively, and thus to exclude influences of the measuring body or measuring site and to evaluate easily and without great effort a product development or the resistance of the radiation protection agent against the performed interactions.

In a separate embodiment of the measuring method, the measurement takes place at different measuring sites having the same distance from the illumination surface to the detection surface. This means in practice that a sun protection factor, which is usually measured on the back, is measured at more practice-relevant measurement sites for radiation protection, such as the face or the forehead or bald spots in the case of sunscreen or at other radiation protection situations, such as hands exposed to radiation. This is done by positioning the optical interface of the measuring device at this site. There must be no change in the measurement procedure or on the device. Until now, a measurement with the "sun simulator" is for ethical and cosmetic reasons (a rectangular redness remains) not performed at naturally exposed sites. Due to the low illumination dose, the inventive method does not cause damage or redness and can be placed, due to the geometry of the optical interface, at almost every location on the skin of a test subject or other skin models.

In an optional further development according to the invention, a plurality of detectors is arranged with identical distance to one of the radiation sources.

In a separate embodiment of the measuring method, the measurement is carried out repeatedly without removing the optical interface of the measuring device, and the temporally consecutive measurements are analyzed. The consecutive determined sun protection factors are also analyzed and the measurement is terminated when the consecutive sun protection factors differ by less than a standard deviation of 1σ from each other, i.e. assume a stable value. Other stability criteria are also contemplated according to the invention. Deviations of the determined sun protection factors can result from the bleaching behavior, the penetration behavior into the measuring body or the skin or technical influences in the measuring device. The method allows, without limitation, a multiple measurement and the analysis is not time-consuming, since the measured values are calculated by a pre-established algorithm from the wavelength-resolved signals obtained from the detector.

In a further development of the method according to the invention for the non-invasive determination of the sun protection factor of a radiation protection agent, a plurality of measurement processes are carried out. The measurement processes are performed at different locations on the measuring body. In the analysis of the sun protection factor of the radiation agent, the measured values obtained at the different sites are averaged. This has the advantage that the locally introduced radiation dose can be minimized when the measuring body is exposed to radiation at a large number of sites. Furthermore, irregularities that may be present as a result of the inhomogeneity of the measuring body or the application of the radiation protection agent and thus may complicate or prevent an accurate measurement of the average sun protection factor, are taken into account in the evaluation.

In a further embodiment of the invention, it is further provided to first perform a measurement on the measuring body in the absence of an applied radiation protection agent. This measurement is then repeated using the same parameters and the same location as the previously performed measurement. This has the advantage that the influence of the measuring body on the effect of the radiation protection agent can be taken into account in the analysis of the protective effect of the radiation protection agent.

To evaluate the influence of external influences on the protective effect of a radiation protection agent, the measurement projects are also repeated. For this purpose, the measuring body to which the radiation protection agent has been applied is measured for the first time between the individual measuring processes. After this first measuring process the measuring body may be exposed to effects influencing the protective effect of the radiation protection agent. The measurement process is then repeated. This happens optimally with the same parameters and at the same position as the first measurement process. The external effects influencing the protective effect of the radiation protection agent may be time, water, abrasion, exposure to radiation or other effects. The effects on the protective effect can be determined through measurements made before and after exposure to the effects. This makes it possible to optimize the protection agent with respect to its resistance to the effects and to thus ensure optimal protection. In one further development of the invention, a measurement may first be performed on the measuring body in the absence of an applied radiation protection agent. Optionally, to determine the influence of the external effect on the protective effect of the radiation protection agent, a measurement may be carried out on the measuring body prior to the first measurement, before the radiation protection agent has been applied to the measuring body.

In a further development of the invention, the radiation is detected spectrally separated for wavelengths or wavelength ranges and then analyzed for the separate wavelengths or wavelength ranges. The spectrally separated wavelengths or wavelength ranges may include UV-A, UV-B, and/or visible light. The spectral separation can be done directly after the radiation source and before the radiation penetrates into the measuring body. Alternatively, the radiation backscattered by the measuring body can be spectrally separated into a plurality of wavelengths or wavelength ranges.

In a further embodiment of the invention, different types of characteristic values are determined from the measured values. These characteristic values are based on different damage functions. These damage functions may include the effect of UV-A radiation or even completely different wavelength ranges on the skin or furthermore to other biological materials (e.g. wood for wood preservatives) due to acute reactions or other damage (for example, DNA strand breaks in living biological material).

This approach has, on the one hand, the advantage that the locally acting radiation dose can be reduced if the spectral separation occurs before the radiation penetrates into the measuring body. On the other hand, this approach has the advantage that the sun protection factor can be calculated independent of the respective spectrum and also independent of the detector characteristic.

In a further development according to the invention, the radiation impinges on a limited area. This area is separate from the detector area.

In a further embodiment of the invention, the sun protection factor of the radiation protection agent is determined according to the formula $$\frac{R_{without}}{R_{with}} = \frac{1}{T^2} = PF^2.$$

In a further embodiment of the invention, the measuring head is cleaned before the measurement process. The cleaning is preferably performed with agents that do not leave residues and/or have no influence on the characteristic of the radiation. This has the advantage that all measurement processes can be carried out under the same optimal conditions. As a result, the radiation dose can be further reduced, since no contamination has to be taken into account for the intensity of the radiation incident on the measuring body.

In a further embodiment of the invention, the individual measurements are carried out for a plurality of distances between the detector and the radiation source. The distances are in this case in a range of 0 mm to 1 mm, preferably from 20 μm to 0.5 mm and more preferably can be varied from 60 μm to 200 μm.

This method has numerous advantages over the prior art. Thus, in the method according to the invention, only a small dose of light below a MED (minimum erythema dose, individually for skin types) or below the maximum permissible irradiation (MZB value, for UV and also other wavelength ranges) is irradiated onto the measuring body. Due to these low doses of light, the process is also suitable for damage-free in-vivo use. This has the advantage that the identical physiological conditions are present during the SPF testing and during application in the sun. The inventive method is also applied non-invasively. Furthermore, the light propagation in the skin is taken into account in the method, thus attaining increased measurement accuracy. The consideration of the physiological properties with a more realistic skin model improves the determination of the sun protection factor in the UVA and in the visible spectral range. Furthermore, an association of in-vivo (human skin) and in-vitro test (→ tissue model=protected item) is possible. Moreover, the process can be used for a very wide wavelength range, and is not limited by lamp spectra, effective erythema spectrum, reactions of the measuring body, and the like. The method according to the invention also offers the possibility of extending the spectral range (SPF is defined only for UVB) for the measurement, since skin reactions (MED) are only found with UVB. Due to the low light dose impinging on the measuring body, no restrictions with regard to the measuring site need to be observed. Even measurements on the sensitive scalp are possible. Furthermore, the influence of substances on the measurement according to the invention is avoided, which influences skin reddening or UV-induced erythema. The inventive method is simpler and more meaningful than the previously known methods and has lower costs.

Furthermore, the object is achieved by a device for non-invasive determination of the sun protection factor of a radiation protection agent, which includes a sensor unit, wherein the sensor unit has at least one radiation source and two detectors, wherein the detectors have different distances to the radiation source, or the sensor unit has at least two radiation sources and a detector, wherein the radiation sources have different distances to the detector, or the sensor unit has one radiation source and one detector, wherein the distance between the radiation source and the detector is variable. The radiation source is constructed to emit light in the area in which the protective effect is to be defined, wherein the distances between the individual radiation sources and the detectors are defined. This range includes in particular the visually visible light (VIS) as well as the UV-B and the UV-A range. The radiation source may emit light even in the NIR range or the IR range. Furthermore, the device according to the invention has a controller for controlling the radiation source, wherein the controller is configured to control the radiation source such that the radiation source emits a maximum light dose with small MED and/or MZB, an analysis unit which is configured to analyze the detected radiation by taking into account respective distances between the radiation source and the detector, and an output unit that outputs the determined value. In an optional further development of the invention, the radiation sources and detectors are arranged in a backscatter arrangement.

In a further embodiment, the device according to the invention can optionally change test parameters such as wavelength, distance r between radiation source and detector and/or spot sizes. This offers the possibility of adapting the measurement parameters and in particular the light dose to the measurement conditions in such a way that the light dose impinging on the measuring body can be minimized without adversely affecting the quality of the analysis.

In a further embodiment of the invention, the distance between a radiation source and a detector is selected so that the detected radiation has passed completely through the layer of the measuring body in which the applied radiation protection agent is located. In a further optional embodiment of the invention, the distance between one or more radiation sources and one or more detectors is between 0 and 1 mm, wherein the distance is selected so that the penetration depth of the radiation is greater than the layer thickness and/or penetration depth of the radiation protection agent into the skin. This ensures that the areas of the measuring body relevant for the determination of the sun protection factor are completely irradiated.

In a further development of the invention, the device has one or more radiation sources and at least one illumination surface, wherein the illumination surface of the radiation sources lies between a circle with Ø7 µm and 1 mm$^2$, preferably between a circle with Ø 100 µm and 250 µm$^2$ and more preferably between a circle with Ø 200 µm and a circle with Ø 400 µm. An optional embodiment of the invention has one or more detectors and at least one detection surface, wherein the detection surface between a circle with Ø 7 µm and 1 mm$^2$, preferably between a circle with Ø 100 µm and 250 µm$^2$ and more preferably between a circle with Ø 200 µm and a circle with Ø 400 µm. As a result, the illumination surface of the radiation sources is, on the one hand, advantageously large enough to introduce enough light, but not too large so that from a certain size only edge region is effective and the etendue is increased. This also limits the light dose required for the analysis.

In a further embodiment of the device according to the invention, the radiation source emits light in accordance with the solar spectrum. Optionally, the analysis unit resolves the measurement spectrally with subsequent weighting according to the typical solar spectrum. The product of light intensity of the radiation source and detector sensitivity then corresponds to the product of solar spectrum and effective and damage spectrum, respectively. This has the advantage that no special radiation sources or detectors are required for the device, since the weighting is done later in the analysis unit and can for determining a sun protection factor be adapted from the predetermined product of solar spectrum and effect or damage spectrum from the existing procedure or also other guidelines for the determination of a sun protection factor.

In a further development according to the invention, the device for measuring the measured quantities has fiber arrangements or optical imaging systems with reducing optics. This significantly improves the spatial resolution and/or allows the use of inexpensive components, which can with the reduction optics produce the same illumination or detection surface.

Figure 1:
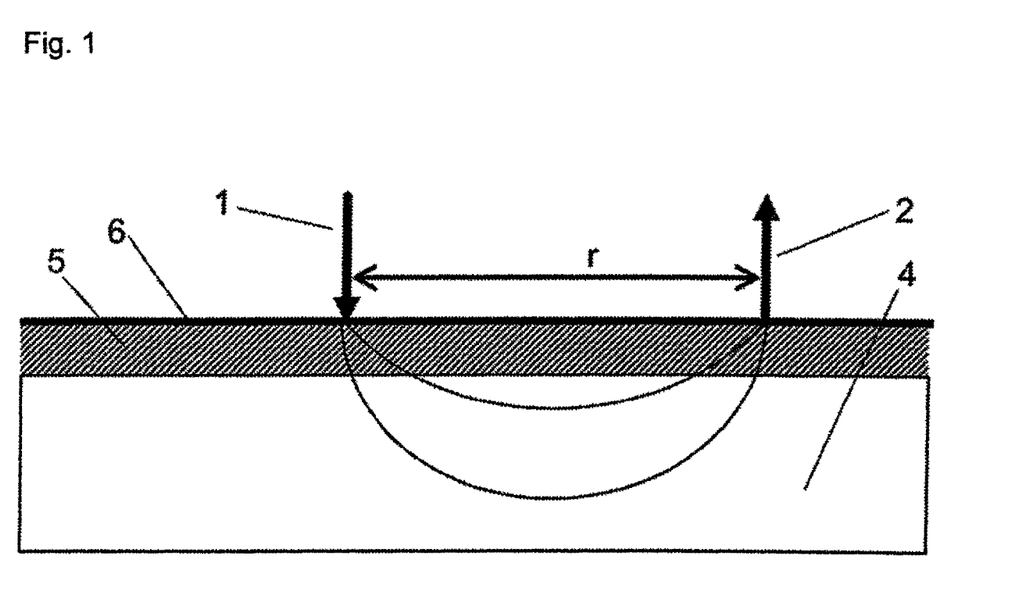
FIG. 1 shows the measuring method according to the invention

Possible Embodiments of the Measuring Arrangements for the Local Distance-Dependent Backscatter:

To measure the distance-dependent backscatter, fiber arrangements or optical systems that image light sources and detectors on the skin surface can be selected. The light from one or more light sources is radiated into the skin over a limited illumination surface, and light backscattered from one or more detection surfaces of the skin is detected by detectors or by a spectrometer. The backscatter must be measured before and after application of the radiation protection product at the same location on the skin. To find the measuring position with the least possible error, a positioning aid is recommended. The spectrally resolved backscatter first results in a spectrum I(λ) of the transmission factor (equation (4)), from which, with equation (5), a standard-compliant protection factor is calculated for example for sunscreen formulations. As an alternative to the spectrally resolved measurement, the spectrum of the light source and the spectral sensitivity of the detectors can be selected so that the measured detector signal is proportional to the integral in equation (5).

Figure 4:
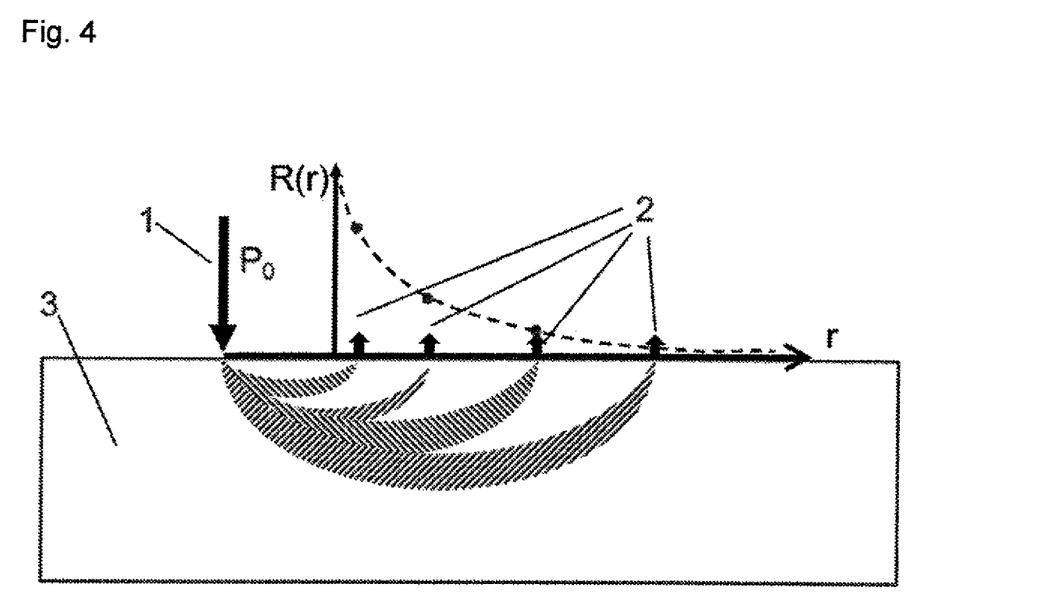
FIG. 4 shows the simultaneous measurement of the backscatter at several distances
Figure 5:
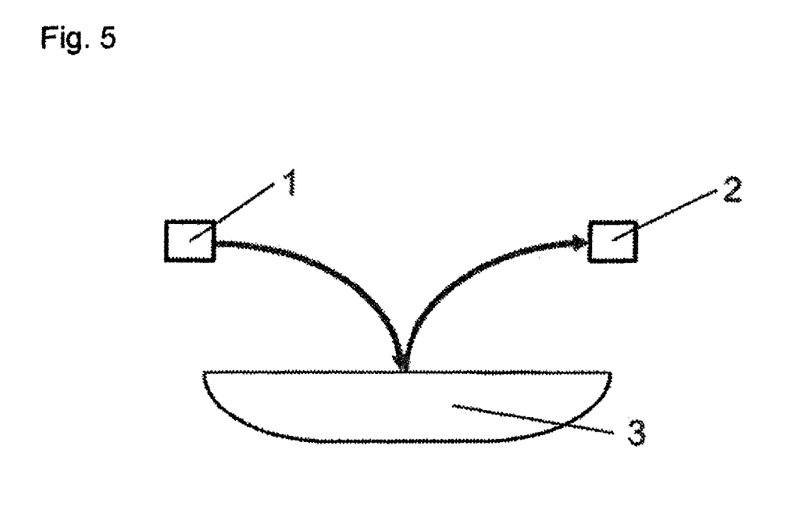
FIG. 5 shows an embodiment according to the invention of the backscatter measurement with respective illumination and detection fibers

A simple arrangement consists, for example, of an illumination fiber and a detection fiber, which are placed on the skin surface at a suitable distance from each other and thus determine the illumination and detection area, 4. A higher light output and the ability to measure simultaneously at several distances between the illumination surface and the detection surface are achieved by a fiber bundle. Detection fibers having identical distance to the illumination fiber are combined on the output side and coupled to a detector. In lieu of the detectors, an imaging spectrometer can be used to simultaneously measure the backscatter spectrum for each distance. In an enhanced embodiment, the backscatter signal is measured in each detection fiber. The variance of the signals allows inferences about the inhomogeneity of the protective properties of the tested radiation protection agent; in addition, erroneous measurements or incorrect application of the radiation protection agent can be detected.

Figure 6:
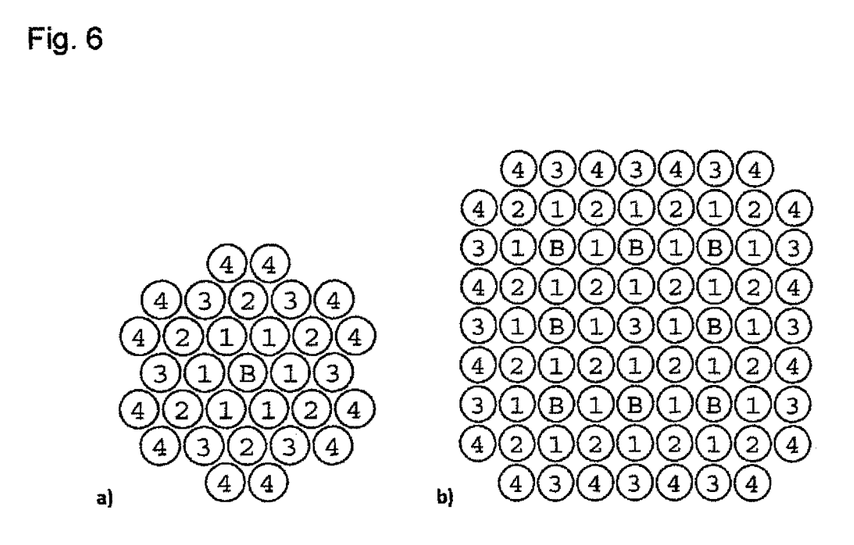
FIG. 6 shows embodiments according to the invention of fiber end faces of fiber bundles for the backscatter measurement

5. By using an arrangement with multiple illumination fibers a), the transmission factor can be averaged over a larger spatial area, or its variance can be determined, Outliers or erroneous measurements can be detected by comparing the measurements at different distances r and at different locations of the skin and excluded from the evaluation. b), several units of the configuration may also be combined into a fiber bundle. B designates here the illumination fiber, 1 to 4 the different fibers at certain distances (1 near, 4 at maximum distance).
  a. The statistical accuracy is further increased by repetitive measurements at different measuring sites either by automatic displacement or by manual displacement of the measuring arrangement.
  b. In general, with the measuring arrangement, light doses can be used that are below a possible damage level.

Practical Considerations for the Measurement:

6. With the non-harmful measurement at any site on the skin can be measured and not only aesthetically acceptable sites, such as the back, as with prior damaging procedures. In particular, the skin on the face can be measured, which is exposed to the greatest risk of damage.
7. By using fiber couplings for the measurement, a stable measurement can be performed with defined spot size in contact and defined numerical aperture or defined light propagation. By a pressure measurement or also by using a support aid with an enlarged surface, the pressure dependence of the measurement can be reduced and the vertical contact controlled, with the latter preventing the optical crosstalk of illumination and detection. By using absorbent or reflective materials between the fibers, optical crosstalk can be reduced, thus further improving channel separation. Erroneous measurements are prevented by using low-fluorescence materials.
8. By using imaging optics for the transmission of illumination and detection optics, both the distance between the optics and the skin surface, as well as the respective spot sizes and numerical apertures can be stably adjusted with a window in the skin contact. With the imaging scale, the spot size can be adapted in each case to suitable detectors.
9. By using interchangeable films affixed on fiber applicators or windows, a spread of radiation protection agent can be prevented and a sterile use can be ensured (is also used in the method described in the document Ruvolo et al., (see p. 3)). For measurements without a film, a suitable cleaning must be performed between the measurements at different measuring sites or test subjects. The contamination of the sensor can be detected by the measuring arrangement itself, for example, by taking a measurement in the free space or into a dark measuring chamber.
10. For an improved measurement, it may be useful to cream the skin with a radiation protection agent without light-attenuating effect (index matching) before measuring with the radiation protection agent.
11. By switching the light source on and off while simultaneously measuring (lock-in technique, etc.), the measuring apparatus can detect the influence of ambient light on the measurement and therefore an erroneous mounting of the measuring arrangement and thus a faulty measurement.
12. The spectral dependence of the re-emission can be determined by using a spectrometer or by illuminating the skin with multiple light-emitting diodes. The measurement for different spectral ranges can be carried out simultaneously or sequentially in order to either adjust the amount of light for a good signal/noise ratio on the detector side or to enable spectral resolution.

The inventive method is further characterized by the following features that can be combined with each other independently:

Before the measurement, the measuring head is positioned perpendicular to the sample surface.

Stray light incident on the measuring area is filtered out for the wavelength range for which the evaluation of the measurement is to take place.

The interfering light is filtered out by modulation techniques, e.g. lock-in techniques.

The measured data are corrected by taking into account the backscatter at the illumination position.

The detected radiation is analyzed separately for individual radiation source/detector pairs.

The determined measured data are analyzed with regard to implausible measured values or erroneously ascertained measured values The measurement processes are carried out in-vivo or in-vitro The sun protection factors are analyzed separately for different wavelength ranges, whereby the different wavelength ranges include light from the spectra UV-A and/or UV-B and/or VIS VIS and/or IR.

The device according to the invention is furthermore distinguished by the following features which can be combined with one another independently of each other:

The measurement is performed with a distance=0 between the radiation source and the detector.

The measurement with distance=0 between the radiation source and the detector is used for calibration. The calibration is necessary only with respect to the spectral position; an intensity need not be calibrated, since the relative measurements with/without a radiation protection agent result in an independence of the measurements from the irradiated intensity, provided that the intensity does not change appreciably between the measurements.

It has means to minimize interference.

Devices are provided which shield the detectors from radiation that was not transmitted through the protective cream and/or the skin or measuring body, respectively.

The analysis unit of the device is configured to detect outliers and erroneous measurements.

EXEMPLARY EMBODIMENTS

In one exemplary embodiment of the method according to the invention, a formulation similar to the radiation protection agent, but without a light-damping effect is first applied to a location on the inside of the forearm. This serves to compare the measurements with/without radiation protection agent and increases the accuracy, but is not mandatory for carrying out the method or for determining a sun protection factor. Thereafter, this measuring site is measured with the measuring device through irradiation with light at a defined surface having a diameter of about 200 µm—generated for example by placing an optical fiber (illumination fiber) with a core diameter of Ø 200 µm. The irradiation has an intensity that does not cause acute damage in the skin, which corresponds to about 5 µW, or below the simple MED, or below the MZB values, or significantly below the values caused by solar irradiation. 1 MED corresponds to the lowest irradiation dose which, when read after 24 hours, caused a distinctly limited erythema (redness) of the skin. This dose varies greatly even among people having the same skin type. 1 MED corresponds to about 250-400 J/m$^2$ (25-40 mJ/cm$^2$) in fair-skinned people of skin type II. Damage can also be prevented by staying below the MZB values. MZB are defined in DIN EN 60825-1 "Safety of Laser Equipment; Part 1: Classification of systems, requirements and user guidelines", which corresponds to the international standard IEC 60825-1. The accident prevention regulation "Laser radiation" (BGV B 2) also contains these values, additions and changes, in particular based on DIN EN 60825-1: 2001-11, listed in BG Information 832 "Operation of Lasers". The underlying limit values originate from the ICNIRP (International Commission on Non-Ionizing Radiation Protection).

This light passes through the skin of the test subject and exits from a detection surface at a predefined distance—for example 60 µm —, which can in turn consist of an attached optical fiber (detection fiber) having a core diameter of 200 µm. To increase the sensitivity or further reduce the illumination intensity, a plurality of detection fibers can be arranged equidistant from the edge of the illumination fiber in an optical measuring head which is in direct contact with the measuring site, and together passed on to a detection device for measuring the intensity. Depending on the magnitude of the intensity and the selected detector, the signal generated by the radiation is amplified by a defined factor, which provides a signal above the noise also for the subsequent measurement of the weaker intensity. The detection is carried out with wavelength resolution. The resolution may be, for example, 1 nm and may be selected depending on the definition of the sun protection factor.

Thereafter, a radiation protection agent of a predetermined type for which the sun protection factor is to be determined is applied on the measurement location. The standards hereby specify a procedure that may or may not be adhered to without affecting the performance of the measurement process. Only the significance of the determined sun protection factor for the application scenarios of the radiation protection agent depends on the type of application.

After application of the radiation protection agent, a further measurement of the same type is carried out at the same measuring site. This completes the measuring cycle after two individual measurements. This similar second measurement is compared to the first measurement, for example, according to the above equation (4). This calculation is carried out with wavelength resolution for the area in which the sun protection factor is to be defined. A sun protection factor SPF is, for example, the SPF, which is valid for sunscreen in the UV-B range and is determined as described in equation (5). The spectra I(λ)—the intensity spectrum of the sun—and E(λ)—the erythema spectrum—are defined in the standard ISO 24444 or in the medical literature [MCKINLAY, A. F., and B. L. DIFFEY (1987) "A reference action spectrum for ultraviolet induced erythema in human skin." In: "Human Exposure to Ultraviolet Radiation" (eds. Passchier, W. F. and B. F. M. Bosnjakovic) Excerpta Medica, Amsterdam, pp. 83-88].

In a modification of the above embodiment, a repetition of the individual measurements during a measurement cycle is also conceivable, wherein the individual measurements are averaged or added (accumulated). The measurement cycle thus includes, for example, 10 to 50 individual measurements without radiation protection agent (or without light attenuation in the radiation protection agent) and an equal number of measurements after application of the radiation protection agent. To avoid other influences, the measurements after application of the radiation protection agent may be detected only after a waiting time after the application of, for example, 2 minutes. Other types of the analysis are also conceivable wherein the wavelength resolved signal values of the individual measurements are all taken into account without being combined into a wavelength-resolved value before analysis (equation (4)).

A modification of one of the preceding embodiments is also a measurement cycle only with a single limited wavelength range, for example with illumination by coupling a 365 nm LED into the illumination fiber. This requires preparatory work in combination with the radiation protection agent and a broader wavelength range which form a basis for correlating the values in the restricted wavelength range with an sun protection factor. It must be ensured as a prerequisite for a correlation that the measurement at 365 nm does not show different spectral light attenuation compared to the comparison measurements for the type of radiation protection agent used during the preparation and measurement. As a further preparatory work, the preceding determination of the sun protection factors is assigned to a measured light attenuation at 365 nm. In the already described measuring cycle with only a single spectrally limited irradiation, the sun protection factors are then determined via this assignment (correlation) by way of comparison with previously known values in the analysis apparatus.

In a modification of one of the preceding exemplary embodiments, a third measurement is to be performed after an interaction of the same kind at the same measuring site. For this purpose, the measuring device is used similarly. The interaction may be, for example, wiping ten times under light pressure and with a moist terry-cloth towel, or other effects caused by light, mechanical, or moisture or combination. This third measurement is evaluated against the first measurement according to equation (4) and yields a 'sun protection factor after interaction' which is compared to the 'sun protection factor without interaction' (determined from the first and second measurements), from which the effect of the interaction on the protective effect can be determined. Such a method with interaction makes sense in tests for water resistance of the radiation protection agent and in accounts on the change of the sun protection factor due to mechanical effects, for example when dressing and changing, which should be part of a product information.

The interaction may also be used to detect the change of the radiation protection agent over time by measuring after a short period of time, for example during the first minutes after application, or over a longer period of time, for example 2 hours after application. The approach is the same. According to the invention, the optical measuring head should be removed after longer periods of time and the replaced at the same location after the predetermined time. Chemical changes of the radiation protection agents or the settling behavior and its effect on the sun protection factor can be detected with such measurements. The individual measurement takes a few seconds, the analysis either takes place immediately (several hundred milliseconds) or the measuring signals of the detectors are buffered.

As an extension of one of the above exemplary embodiments, third measurements are carried out periodically, for example every 5 seconds, and analyzed until the deviation of the successive values lies below the simple standard deviation, i.e. shows stable values. Such an evaluation takes place in the analysis unit, which terminates the measurement when the stable values are reached and signals this to the user.

In a modification of one of the preceding exemplary embodiments, a further measurement is also to be carried out at another measuring site in the same way. The sun protection factor of the same radiation protection agent with similar application at different locations can thus be compared. Likewise, according to the invention, a first measurement (individual measurement without radiation protection agent) at the additional measuring site can form the basis for the analysis of the further measurement.

What is claimed is:

1. A method for non-invasive determination of a sun protection factor (SPF) of a radiation protection agent, comprising:
controlling with a controller an emitted light intensity of at least one radiation source for irradiating a measuring body during a single individual measurement with radiation having a wavelength range extending over a spectral range in which a protective effect of the radiation protection agent on the measuring body is to be defined with a maximum light dose that is smaller than a MED (minimal erythema-producing dose) and/or a MZB (maximum permissible irradiation), wherein the wavelength range in which the protective effect of the sun protective effect of the radiation protection agent on the measuring body is to be detected is the UVA-range and/or the UVB-range and/or the IR-range and/or the VIS-range,
detecting the radiation emitted by the at least one radiation source in at least one detector during a measurement cycle of the determination of the SPF comprising at least two individual measurements,
wherein a distance between the at least one radiation source and the at least one detector of the first individual measurement is different from the distance between the at least one radiation source and the at least one detector of the second individual measurement;
analyzing the detected radiation while taking into account the distance between the at least one radiation source and the at least one detector during the first and second individual measurement; and
outputting a value determined for the SPF.

2. The method of claim 1, wherein for a measuring process, several measurement cycles having an identical position on the measuring body are performed, and/or a measurement cycle comprises several individual measurements having an identical distance from illumination surface to detection surface, wherein the individual measurements are performed at the identical distance at different positions on the measuring body, wherein the measurement cycles are repeated until the sun protection factor determined from the radiation of the at least one radiation source and the radiation detected in the at least one detector differs from previously determined sun protection factors by less than one standard deviation σ, wherein one standard deviation is defined as, with $$\sigma = \sqrt{\frac{1}{N-1}\sum_{i=1}^{N}(x_i - \bar{x})^2},$$

with N being the number of measurement cycles, $x_i$ being the previously determined sun protection factors, and $\bar{x}$ being a mean value of the previously determined sun protection factors during the measurement cycles.

3. The method of claim 1, wherein for determining the SPF several measurement processes are carried out at locations of the measuring body, which have a different exposure to the radiation protection agent, wherein the measurement processes are preferably carried out at an identical position on the measuring body.

4. The method of claim 1, wherein several measurement processes are carried out at different positions on the measuring body, and wherein for determining the SPF of the radiation protection agent, measured values determined at the different positions are averaged.

5. The method of claim 1, wherein measuring processes are carried out repeatedly, wherein between the measuring processes, the measuring body to which the radiation protection agent is applied, is exposed to effects affecting the protective effect of the radiation protection agent, with these effects including abrasion, water, time and/or the exposure to radiation, and/or a measurement process is carried out without prior application of the protection agent on the measuring body and a measurement process is carried out with prior application of the protection agent on the measuring body.

6. The method of claim 1, wherein the detected radiation is recorded and evaluated spectrally separated for wavelengths or wavelength ranges, wherein the spectral separation comprises the wavelength ranges UV A, UV-B and/or the visible light, and/or wherein the radiation is irradiated onto a limited area which is separated from a detector area.

7. The method of claim 1, wherein different types of characteristic values are determined from the measured values, wherein the characteristic values are based on different damage functions.

8. The method of claim 1, wherein the sun protection factor of the radiation protection agent is determined according to the formula $$\frac{R_{without}}{R_{with}} = \frac{1}{T^2} = SPF^2,$$

wherein $R_{without}$ is a detected backscatter without the radiation protection agent, $R_{with}$ is the detected backscatter with the radiation protection agent applied, T is a wavelength-dependent scalar transmission factor indicating the light attenuation due to the protection agent, and SPF is the sun protection factor.

9. The method of claim 1, wherein the individual measurements are carried out for several distances which are varied at least over a range of 0 mm to 1 mm, preferably from 20 µm to 0.5 mm and more preferably from 60 µm to 200 µm.

10. The method of claim 1, wherein the wavelength range in which the protective effect of the sun protective effect of the radiation protection agent on the measuring body is to be detected is the UVA-range.

11. A device for non-invasive determination of a sun protection factor (SPF) of a radiation protection agent, comprising:
- a sensor unit comprising
    - at least one radiation source and at least one detector, wherein respective defined distances between the at least one radiation source and the at least one detector are variable;
- a controller connected to the at least one radiation source for controlling the at least one radiation source to emit during a single individual measurement light extending over a spectral range in which a protective effect of the radiation protection agent is to be defined, with a maximum light dose that is smaller than a MED (minimal erythema-producing dose) and/or a MZB (maximum permissible irradiation), wherein the spectral range in which the protective effect of the sun protective effect of the radiation protection agent is to be detected is the UVA-range and/or the UVB-range and/or the IR-range and/or the VIS-range;
- said controller adapted to detect the light emitted by the at least one radiation source in the at least one detector during a measurement cycle of the determination of the SPF comprising at least two individual measurements, wherein the defined distance between the at least one radiation source and the at least one detector of the first individual measurement is different from the defined distance between the at least one radiation source and the at least one detector of the second individual measurement; and
- said controller further adapted to analyze a radiation detected by the at least one detector by taking into account the respective defined distances between the at least one radiation source and the at least one detector during the first and second individual measurements; and to output a value determined for the SPF.

12. The device of claim 11, wherein the radiation protection agent is applied on a measuring body in form of a layer, and wherein the device is configured to change experimental parameters selected from at least one of wavelength, distance r between a radiation source and a detector, and a spot size, and/or wherein the distance between the respective radiation source and the respective detector is selected such that the detected radiation has previously entered the measuring body at least partially in depth through the layer.

13. The device of claim 11, comprising at least one radiation source and at least one illumination area, wherein the illumination area is located inside a circle with Ø 7 µm and 1 mm$^2$, preferably between a circle with Ø 100 µm and 250 µm$^2$, and more preferably between a circle with Ø 200 µm and a circle with Ø 400 µm, and/or wherein the distance between one or more radiation sources and one or more detectors is between 0 and 1 mm, and wherein the distance is selected so that a penetration depth of the radiation is greater than a layer thickness of the radiation protection agent and/or a penetration depth of the radiation protection agent into the skin.

14. The device of claim 11, comprising one or more detection areas that are joined onto a single detector, wherein the joined detection areas are located between a circle with Ø 7 µm and 1 mm$^2$, preferably between a circle with Ø 100 µm and 250 µm$^2$, and more preferably between a circle with Ø 200 µm and a circle with Ø 400 µm.

15. The device of claim 11, wherein the one or more radiation sources emit light commensurate with a typical solar spectrum or wherein the controller spectrally resolves the detected radiation followed by weighting in accordance with the typical solar spectrum, such that a product of light intensity of the radiation source and detector sensitivity corresponds to a product of the typical solar spectrum and an effective or damage spectrum.

16. The device of claim 11, wherein the sun protection factor of the radiation protection agent is determined as an averaged value from a plurality of measurements from one or more measuring sites.

* * * * *